(12) United States Patent
Le Bras-Roulier et al.

(10) Patent No.: US 6,344,187 B1
(45) Date of Patent: Feb. 5, 2002

(54) COSMETIC COMPOSITION IN THE FORM OF A SOFT PASTE AND PROCESS FOR PREPARATION OF SAME

(75) Inventors: Véronique Le Bras-Roulier, Paris; Dolorès Miguel-Colombel, L'Hays-les-Roses; François Pradier, Fotenay aux Roses, all of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/174,243

(22) Filed: Oct. 16, 1998

Related U.S. Application Data

(63) Continuation of application No. 08/964,018, filed on Nov. 4, 1997, and a continuation of application No. 08/583,553, filed on Jan. 5, 1996.

(30) Foreign Application Priority Data

Jan. 5, 1995 (FR) .............................. 95-00072

(51) Int. Cl.$^7$ ........................ A61K 7/025; A61K 47/44; B29C 47/60
(52) U.S. Cl. ...................... 424/64; 424/63; 264/211.21; 264/211.23
(58) Field of Search ............................ 424/61, DIG. 5, 424/63–64; 264/176.1, 211.21, 211.23, 175

(56) References Cited

U.S. PATENT DOCUMENTS

| | | |
|---|---|---|
| 3,937,811 A | 2/1976 | Papantoniou et al. |
| 4,871,536 A | 10/1989 | Arraudeau et al. |
| 4,994,264 A * | 2/1991 | Verdon et al. |
| 5,053,220 A | 10/1991 | Arraudeau et al. |
| 5,154,916 A | 10/1992 | Arraudeau et al. |
| 5,437,859 A | 8/1995 | Ser et al. |
| 5,679,361 A * | 10/1997 | Pradier et al. |
| 5,700,410 A * | 12/1997 | Nakamichi et al. |
| 5,897,869 A * | 4/1999 | Roulier et al. |
| 5,830,444 A | 11/1999 | Miguel |

FOREIGN PATENT DOCUMENTS

| | | |
|---|---|---|
| DE | 3243017 | 5/1984 |
| DE | 3744352 | 7/1989 |
| EP | 524892 | 1/1993 |
| EP | 530084 | 3/1993 |
| EP | 605284 | 7/1994 |
| EP | 609132 | 8/1994 |
| EP | 667146 | 8/1995 |
| FR | 2486800 | 1/1982 |
| FR | 2715306 | 7/1995 |
| GB | 2167301 | 5/1986 |
| GB | 2216797 | 10/1989 |
| JP | 8-99853 | 4/1996 |
| WO | WO 9116879 | 11/1991 |
| WO | WO94/14402 | 7/1994 |

* cited by examiner

Primary Examiner—Edward J. Webman
(74) Attorney, Agent, or Firm—Finnegan, Henderson, Farabow, Garrett & Dunner, L.L.P.

(57) ABSTRACT

A cosmetic composition which is presented in the form of a soft paste, which is capable of being used as lipstick and comprising a fatty phase in which waxes are present. A process for the preparation of this composition is also disclosed.

4 Claims, No Drawings

COSMETIC COMPOSITION IN THE FORM OF A SOFT PASTE AND PROCESS FOR PREPARATION OF SAME

This is a continuation division of application Ser. No. 08/964,018, filed Nov. 4, 1997, which is incorporated herein by reference and is a continuation of Ser. No. 08/583,553 filed Jan. 5, 1996.

The present invention is directed to a composition provided in the form of a soft paste, in particular to a cosmetic composition which can be used for making up the lips, or as a composition for treating the hair and/or the lips.

Cosmetic compositions which can be applied to the lips as treatments or make-up products, such as lip color compositions, generally contain fatty substances and waxes, and optionally contain additives and pigments. Such compositions which are presented in the form of a soft paste and which are capable of being applied after collecting with the aid of an applicator, for example a brush, are in particular known.

These compositions may contain waxes which confer on them notable qualities with regard to the consistency, unctuosity and retention of the applied film.

In order to introduce relatively large quantities of waxes into these compositions, a preparation process was proposed which consisted of preparing the mixture of the constituents, heating the mixture to a temperature where the waxes are at least partially melted, and then subjecting the mixture to a blending operation during at least part of its cooling. Crystallization of the waxes in a form which allowed the production of a soft and easily removable paste was thus observed.

It was found, however, that some waxes did not make it possible to obtain a cosmetic composition having optimum and constant cosmetic qualities during their storage, in particular when this storage was performed, even partially, at a temperature greater than a customary temperature of the order of 20–25° C.

Indeed, depending on the nature of the waxes present in the composition, it was possible to observe, in some cases, a modification of the viscosity of the composition which could result in substantial hardening of the composition and in problems of application.

An object of the present invention is to overcome these disadvantages and to provide a cosmetic composition having optimum cosmetic qualities during the whole of its storage, inter alia, a viscosity which is practically constant over time, regardless of the temperature, or the temperature changes, to which it is subjected.

One subject of the present invention is therefore a cosmetic composition provided in the form of a soft paste and comprising a fatty phase in which one or more waxes are present, the composition being characterized in that at least 95% of the waxes have a temperature at the onset of melting which is greater than or equal to 50° C.

Another subject of the invention is a process for the preparation of such a cosmetic composition, in which at least a portion of the various constituents of the composition, including the waxes, is heated to a temperature at which the waxes melt at least partially. The remainder of the constituents are added where appropriate and then the mixture obtained is blended during at least part of its cooling.

The present invention allows the production of compositions which remain stable over time, that is to say, whose viscosity remains practically constant. These compositions possess a novel soft texture and exhibit, after application, high retention and high brilliance.

The composition according to the invention therefore comprises a fatty phase in which one or more waxes may be present, it being necessary for at least 95% of the waxes to have a temperature at the onset of melting which is greater than or equal to 50° C.

"Temperature at the onset of melting" is understood in the present description to mean the temperature at which a wax begins to melt.

This temperature can be determined by DTA (differential thermal analysis) which makes it possible to obtain the thermogram (or the melting curve) of the wax considered. The temperature at the onset of melting corresponds to the temperature at which a notable change in slope can be observed in the thermogram. The melting point, for its part, represents the minimum point of the thermogram.

Without being limited by the present explanation, it can be assumed that the change in viscosity observed during the storage of some cosmetic compositions is linked to the modification in the form in which the waxes crystallize.

Indeed, during the manufacture of the composition of the present invention, the waxes are crystallized in a certain form which will allow the production of a soft paste.

During a substantial rise in temperature during their storage, the waxes may melt at least partially, and then recrystallize in a form different from the initial crystalline form. This second form no longer allows a soft paste to be obtained but is capable of leading to a paste with a higher viscosity and therefore with a more rigid consistency.

Thus, by choosing at least 95% of the waxes present in the composition from those waxes having a temperature at the onset of melting greater than or equal to 50° C., a composition can be obtained whose viscosity remains constant. Preferably, waxes are used whose temperature at the onset of melting is greater than 65° C. It is also preferable to choose 100% of the waxes from those whose temperature at the onset of melting is greater than or equal to 50° C.

The waxes capable of being used in the present invention, that is to say which make it possible to maintain a viscosity of the cosmetic composition constant, may be of any type, in particular, of inorganic, animal, plant or synthetic origin.

There may preferably be mentioned Carnauba wax, some polyethylene waxes, and some microcrystalline waxes, such as that sold by Tisco under the name "Tisco Wax 88".

These waxes may be used alone or in the form of a mixture.

These waxes may also be used in a mixture with waxes whose temperature at the onset of melting is less than 50° C.; it being understood that these second waxes cannot represent more than 5% by weight of the total waxes.

The composition according to the invention preferably comprises, in total, 10–60% by weight of wax relative to the final weight of the composition. More preferably, the composition comprises 15–35% by weight of wax relative to the final weight of the composition.

The fatty phase may, in addition, comprise other fatty constituents such as oils. There may preferably be mentioned:

mineral oils such as paraffin oil or liquid paraffin;

animal oils such as perhydrosqualene or arara oil;

vegetable oils such as sweet almond, calophyllum, palm, castor, avocado, jojoba, olive or cereal germ oil;

esters of lanolic acid, oleic acid, lauric acid, stearic acid or myristic acid, for example;

alcohols such as oleyl alcohol, linoleyl or linolenyl alcohol, isostearyl alcohol or octyl dodecanol;

acetylglycerides, octanoates, decanoates or ricinoleates of alcohols or of polyalcohols.

These fatty constituents preferably represent 40–90% by weight of the composition, and more preferably 65–85% by weight of the composition.

In a known manner, there may be added to the composition according to the invention a pulverulent colouring agent such as carbon black, chromium or iron oxides, ultramarines, manganese pyrophosphate, ferric blue, titanium dioxide, pearlescent agents, which are generally used in the form of a mixture with coloured pigments, or certain organic colorants, which are generally used in the form of a mixture with coloured pigments or which are commonly used in the cosmetic industry.

These colouring agents are preferably present in a quantity 0 to 20% relative to the total weight of the composition.

Inorganic or organic pulverulent fillers may also preferably be added in a quantity of 0 to 40% relative to the total weight of the composition.

These pulverulent fillers may preferably be chosen from talc, micas, kaolin, zinc or titanium oxides, calcium or magnesium carbonates, silica, spheric titanium dioxide, glass and ceramic beads, metallic soaps derived from carboxylic acids having 8–22 carbon atoms, nonexpanded synthetic polymer powders, expanded powders and powders of natural organic compounds such as cereal starches, crosslinked or otherwise.

There may also preferably be added any additive customarily used in the cosmetic industry, such as antioxidants, perfumes, preservatives, as well as cosmetic and/or pharmaceutical active agents such as vitamin derivatives, essential fatty acids, sphingocerils, fat-soluble sunscreens, anti-inflammatory agents or oily plant extracts, or even fat-soluble polymers, and/or silicone oils and/or gums such as dimethylpolysiloxanes. These additives are preferably present in an amount of 0–10% by weight relative to the total weight of the composition.

In order to prepare the composition according to the invention, it is possible to first prepare a premix comprising at it least a portion of the various constituents of the composition, including at least the wax according to the invention, to heat this premix at a temperature at which the wax melts at least partially, to add, where appropriate, the remainder of the constituents, and then to blend the mixture obtained during at least part of its cooling down to room temperature. It was indeed found that when the mixture is blended during at least part of its cooling, so as to create shearing regions, a composition is obtained which is presented in the form of a homogeneous and soft paste. It would seem, however, without being limited to this explanation, that under these conditions, the wax crystallizes in the form of fine crystals, which would explain that the composition remains in the form of a soft paste.

The heating operation may be carried out according to any known technique. The blending operation may be carried out, for example, in a roll mill incorporating two rolls rotating in opposite directions between which the paste passes, or alternatively in a mixer-extruder which makes it possible to obtain a paste of highly constant quality in a reproducible manner. Furthermore, it is possible, by adapting the outlet die of the mixer-extruder, to package the composition on-line at the outlet of the die.

In a preferred embodiment of the invention, the mixing, heating and/or blending/shearing, or even cooling, operations are performed in one or more extruders arranged in succession one after the other; more preferably, the operations are performed in a single twin-screw extruder.

Indeed, the composition obtained after extrusion has a special smoothness, and offers some sensation of sliding when it is applied to the skin; while avoiding the appearance and the sensation of oily fat.

The conditions under which the extrusion may be carried out are described in Patent Application FR-A-2715306, whose disclosure is fully incorporated in the present application by reference.

A composition for topical use is thus obtained which may be applied to the skin and/or to the lips as a make-up product, a lip color composition for example, or as a treatment product.

The composition of the invention is in the form of a soft paste. The viscosity of the composition of the invention can be measured. This is not the case, for example, for compositions in the form of a stick.

The dynamic viscosity, at 25° C., preferably ranges from 3 to 35 Pa.s, measured with the aid of a CONTRAVES TV rotational visometer, equipped with an MS-R4 moving body, at a frequency of 60 Hz.

The invention is illustrated in greater detail in the following examples, in which the percentages are given by weight relative to the composition.

The viscosity measurements were carried out at 25° C., with the aid of a Contraves rotational viscometer equipped with an MS-R4 moving body.

The measurements of the melting characteristics of the waxes were performed by DTA (differential thermal analysis) under the following conditions: heating from 25 to 110° C., at a rate of 1° C./minute.

EXAMPLE 1

Composition According to the Invention

A lip color composition having the following composition was prepared:

| | |
|---|---|
| Liquid paraffin | 22.5% |
| Lanolin oil | 23.5% |
| Isopropyl lanolate | 24% |
| Microcrystalline wax (nonpolar mineral wax sold by Tisco, under the name "Tisco wax 88") | 20% |
| Fillers (titanium oxide, mica) | 3.5% |
| Pigments | 6.5% |

These various ingredients were mixed at about 100° C. and the mixture was introduced at the head of a twin-screw extruder. The extrusion was carried out under the following conditions:

Inlet temperature: 100° C.

Outlet temperature: 30° C.

Residence time: about 3 minutes

Screw speed: 350 revolutions/min

A soft paste was obtained at the outlet which was presented in the form of a single, stable and homogeneous phase and which was collected with the aid of a brush for its application.

After application, this paste was considered to have satisfactory qualities in relation to smoothness and sliding and did not have an oily texture.

After six months of storage at 25° C. and 47° C., the following viscosity measurements were obtained:

Storage at 25° C.: 90 poises (9 Pa.s)

Storage at 47° C.: 92 poises (9.2 Pa.s)

It was therefore observed that the composition according to the invention retained practically the same viscosity after storage at room temperature or at a high temperature.

After six months of storage at 47° C., the appearance of the paste did not change and could still be collected with the aid of a brush in order to be applied to the skin. The wax used in this composition had a temperature at the onset of melting of the order of 65–75° C. and a melting point of about 91–93° C.

EXAMPLE 2

Comparative Example

A lip color composition having the following composition was prepared:

| | |
|---|---|
| Liquid paraffin | 22.5% |
| Lanolin oil | 23.5% |
| Isopropyl lanolate | 24% |
| Microcrystalline wax (nonpolar mineral wax sold by RMC, under the name "Feruwax 30540") | 20% |
| Fillers (titanium oxide, mica) | 3.5% |
| Pigments | 6.5% |

The lip color composition was prepared in the same manner as in Example 1 and a soft paste was also obtained which was capable of being collected with the aid of a brush.

After storage for two months, the following viscosity measurements were obtained:

Storage at 25° C.: 80 poises (8 Pa.s)

Storage at 47° C.: 175 poises (17.5 Pa.s)

It was therefore observed that after only two months of storage at 47° C., a highly thickened composition was obtained which could no longer come out of the applicator.

The wax used, although having a melting point of about 69–71° C., had a temperature at the onset of melting of the order of 45–46° C.

Thus, the mere fact of choosing a wax whose melting point is of the order of the storage temperature is not sufficient in itself to make it possible to maintain a constant viscosity for the composition and therefore its suitable cosmetic properties.

What is claimed is:

1. A process for preparing a composition in the form of a soft paste, said composition comprising a fatty phase in which at least one wax is present, wherein at least 95% of said at least one wax has a temperature at onset of melting which is greater than or equal to 50° C., which process comprises heating at least a portion of the constituents of said composition, including said at least one wax, to a temperature at which said at least one wax melts at least partially, adding the remaining constituents to said heated composition, and then cooling the resulting mixture to room temperature, wherein during at least part of said cooling operation the resulting mixture is blended.

2. A process according to claim 1, wherein said blending operation is carried out in a roll mill or in an extruder.

3. A process according to claim 1, wherein said heating, adding or blending operations are carried out in one or more extruders, wherein when more than one extruder is used, said extruders are arranged in succession.

4. A process according to claim 1, wherein said heating, adding, and blending operations are carried out in a single twin-screw extruder.

* * * * *